(12) United States Patent
Kovacs (10) Patent No.: US 10,675,416 B2
(45) Date of Patent: Jun. 9, 2020

(54) RETRACTABLE SYRINGE (71) Applicant: David Harold Kovacs, Nanalmo (CA)

(72) Inventor: David Harold Kovacs, Nanalmo (CA)

( * ) Notice: Subject to any disclaimer, the term of this patent is extended or adjusted under 35 U.S.C. 154(b) by 116 days.

(21) Appl. No.: 16/104,135

(22) Filed: Aug. 17, 2018

(65) Prior Publication Data

US 2020/0054841 A1  Feb. 20, 2020

(51) Int. Cl.
*A61M 5/178*  (2006.01)
*A61M 5/50*  (2006.01)
*A61M 5/32*  (2006.01)

(52) U.S. Cl.
CPC ........ *A61M 5/3234* (2013.01); *A61M 5/3204* (2013.01); *A61M 5/3221* (2013.01); *A61M 5/5086* (2013.01); *A61M 2005/3226* (2013.01); *A61M 2005/3238* (2013.01)

(58) Field of Classification Search
CPC ........ A61M 5/5086; A61M 2005/3238; A61M 2005/3235; A61M 2005/3226; A61M 5/3221; A61M 5/3204; A61M 5/3234; A61M 2005/3261
See application file for complete search history.

(56) References Cited

U.S. PATENT DOCUMENTS

| | | | | |
|---|---|---|---|---|
| 6,206,853 B1 * | 3/2001 | Bonnet | ................. | A61M 5/326 604/110 |
| 6,852,096 B1 * | 2/2005 | Pouget | ................ | A61M 5/3257 604/110 |
| 6,872,190 B1 * | 3/2005 | Denis | .................... | A61M 5/326 604/110 |
| 7,004,929 B2 * | 2/2006 | McWethy | ............. | A61M 5/326 604/110 |
| 9,662,456 B2 * | 5/2017 | Woehr | ............... | A61M 5/31511 |
| 10,130,768 B2 * | 11/2018 | Dungar | ................. | A61M 5/284 |
| 10,485,929 B2 * | 11/2019 | Fuke | ................. | A61M 5/31576 |
| 2003/0229314 A1 * | 12/2003 | McWethy | ............. | A61M 5/326 604/197 |
| 2005/0096595 A1 * | 5/2005 | Restelli | ................. | A61M 5/326 604/198 |
| 2005/0148943 A1 * | 7/2005 | Chevalier | ............. | A61M 5/326 604/198 |
| 2008/0262423 A1 * | 10/2008 | Ingram | ............. | A61M 5/31501 604/110 |
| 2009/0270803 A1 * | 10/2009 | Brunel | .................. | A61M 5/326 604/110 |
| 2010/0179487 A1 * | 7/2010 | Woehr | ............... | A61M 5/31511 604/196 |
| 2011/0092915 A1 * | 4/2011 | Olson | ................. | A61M 5/3129 604/198 |
| 2012/0116319 A1 * | 5/2012 | Grunhut | ............. | A61M 5/2033 604/198 |

(Continued)

*Primary Examiner* — Matthew F Desanto (57) ABSTRACT

An automatic retractable syringe comprised of a syringe inside a compressed spring loaded locking safety sheath that moves into a protective position over the needle of the syringe that is triggered by the depression of the plunger, causing the positional locking mechanism to displace from its initial position and activate a compressed spring that expands, moving the locking safety sheath into its protective position and locks the sheath, preventing further movement of the locking safety sheath. An optional fusing system acts to permanently fix the locking mechanism in place to further secure the locking safety sheath in the protective position.

9 Claims, 5 Drawing Sheets

(56) References Cited

U.S. PATENT DOCUMENTS

| | | | | |
|---|---|---|---|---|
| 2013/0204229 A1* | 8/2013 | Olson | ................ | A61M 5/31511 604/506 |
| 2014/0039406 A1* | 2/2014 | Verespej | ................ | A61M 5/24 604/194 |
| 2015/0148749 A1* | 5/2015 | Cohn | ................ | A61M 5/3257 604/198 |
| 2015/0320935 A1* | 11/2015 | Dungar | ................ | A61M 5/284 604/91 |
| 2016/0228652 A1* | 8/2016 | Cabiri | ................ | A61M 5/3234 |

\* cited by examiner

RETRACTABLE SYRINGE

BACKGROUND OF THE INVENTION

Field of Endeavor

An automatic, single use, retractable syringe, also known as a retractable safety syringe. This invention relates to a syringe with safely features to protect the handler from being injured by the needle after use. The field that most suits this invention and its applications is the Medical Field. This retractable syringe would be most appropriately used in the medical field, and for distribution to those suffering from drug addiction, requiring a syringe that automatically locks in a protective position for the safety of others. This retractable syringe is used for the injection of materials into humans, animals, or for use when a syringe is required and a potential danger or contaminant risk from the syringe is probable.

Background of the Art

With the increase in transmission of diseases from needle sharing due to the rising opioid crisis, there has been a strong movement to supply clean needles to those suffering from drug addiction. Unfortunately, this has resulted in an increase in discarded infectious needles in parks and other public areas that create a significant danger to the general public. The spread of infectious diseases, such as AIDS and Hepatitis can occur when an infectious needle from a drug user is discarded in a public area and comes into contact with the general public in a number of ways. The dangers to public safety regarding this issue are very well known and documented.

The dangers of a discarded infectious needle injuring a member of the public is a growing problem, as more needles are handed out to drug users to prevent cross infection between drug users due to needle sharing. Among the most vulnerable in the population to be in danger of contact with a discarded infectious needle are children, custodians, parks workers, garbage men, and other civil servants, as children may not be able to identify the danger, and custodians, parks workers, and other civil servants are often challenged with the task of removing and disposing of the discarded needles.

The increase in the number of discarded syringes and the frequency of contact with them in cities and towns is quickly becoming an epidemic and has resulted in the need for syringes that can be handled safely when they are improperly discarded after use.

There are several different retractable needles that have been developed, but many of these designs have failed to make it to market, as they are too complex in design, are too expensive to make, or have design flaws that cause the needle to retract too quickly causing injury to the user, or have design flaws that impede the proper functions of the syringe.

Many of the retractable needle designs that have been patented have opted for an internal locking mechanism, which is a design that poses several problems. For example, in order to design a retractable syringe with a locking mechanism that is built into the syringe, many of the working parts have to be very small in order to fit the locking mechanism into the small spaces inside the syringe itself. These tiny parts can be subject to structural failure.

In addition, the increase of surface area and the mechanics involved with constructing these syringes can result in increased chance of contamination of the syringe during the process of manufacturing the syringes and this can also create weak points in which leaking from the barrel and other areas of the syringe can occur.

Among the most common deficiencies in the design of retractable syringes in the past has been that of problems regarding reliability, ease of use, and cost, as these syringes have to be mass-produced by the millions. The need for high speed production of syringes demands a design that is easily molded and assembled, which means that retractable syringes with numerous small internal parts requiring extensive effort to assemble are not likely to be produced at a competitive cost.

PRIOR ART

Regarding prior art, there are many retractable syringe designs available, Each of these designs have some general and obvious features that are related to each other. For example, they all contain a plunger with a rubber plunger head, barrel, needle adapter, needle hub, needle or shaft with a beveled end, measurement scale, finger flange, and a protective cover, all of which are implied and understood as part of the basic and obvious features of a syringe, and are understood as obvious features of this invention.

Further to this, many of the prior art utilize the obvious component of a compressed spring as a method of automatic retraction for retractable syringes.

The first true hypodermic needle was created by Alexander Wood in 1853 and its use became widely used by the medical community shortly after. Since then, hypodermic needles have been significantly improved in efficiency, usefulness, and safety of use. The materials that are used to make syringes have also changed during this time in order to prevent leaks and reduce chances of infections, in order to make the device more reliable. In the late nineteenth century, biocompatible materials, such as improved plastics, rubber, and glass were developed to further improve the safety and efficacy of the syringe.

Prior art has not mentioned the use of a retractable syringe for the safety of the public after the user has discarded the syringe in an area in which the general public may come into contact with it and become contaminated through secondary handling of the syringe.

The designs of prior art are more complex than this invention, making them more difficult to manufacture and therefore more expensive to make due to small and delicate parts as a consequence of their internal design, where the locking mechanism and retraction occurs inside the small area at the front of the barrel.

The design of prior art, having the components of the locking mechanism inside the barrel increases the internal surface area in which contamination might form and may reduce the sterile conditions of the interior working parts of the syringe, which is not the case with this invention, as the mechanisms that cause retraction do not interfere with the normal operation of the syringe.

Prior art fails to address the need for a retractable syringe to be identifiable by sight for safety reasons. Many of the prior art cannot readily be identified by sight alone, as the working parts of the syringe are internalized and this reduces the ability to discern them from a conventional syringe.

Prior art has shown difficulty designing an effective way of controlling the retraction of the syringe with minimal effort in order to prevent splatter and backsplash, or pain from needle retraction while the needle is still in the patient.

Prior art has failed to introduce a design for a fusing system to permanently fix the needle in place subsequent to use of the syringe in order to ensure the locking mechanism will not come undone and cause the needle to become exposed.

There are several differences between prior art and this invention, such as the internal design of the retraction method compared to the external design of this invention and the use of the optional fusing system that prior art does not have. Several of the prior art use different methods of retraction and locking of the needle.

Notable differences prior art uses are, use of an air bleed hole to control retraction force, Luer-lock thread designs, using a needle tilt method of locking, which can be unreliable as the needle could dislodge, Plunger locks, internal mechanisms with side plunger designs, no optional fusing system, no locking safety sheath, one piece design, different locking mechanisms, situating the barrel on the side instead of being in line with the syringe in design, dual chamber designs, and the use of gas to retract the needle instead of using a spring.

Prior art found having relation in relevance to this invention are listed below:

| Pat. No. | Invention Title in The Canadian Patents Database |
| --- | --- |
| 2,111,208 | Syringe with retractable needle and closed barrel |
| 2,356,199 | Retractable hypodermic needle assembly and method for making the same |
| 2,178,937 | Retractable syringe with a closed barrel |
| 2,780,168 | Clinical Syringe |
| 2,142,731 | Retractable syringe with a closed barrel |
| 2,797,207 | Syringe Barrel Adapter and Needle Assembly |
| 2,548,187 | Retractable Syringe |
| 2,218,478 | Tamperproof Retractable Syringe |
| 2,920,509 | Retainer for Retractable Needle Assemblies and Syringes |
| 2,692,968 | Prefilled Retractable syringe, Plunger and Needle Assembly |
| 2,835,950 | Modular Gas-Actuated Retractable Needle Assembly |
| 2,784,437 | Retractable syringe with improved Delivery Efficiency and Locking system |
| 2,621,479 | Single Use Safety Syringe Having a Retractable Needle |
| 2,838,559 | Prefilled Retractable Syringe, Plunger and Needle Assembly |
| 2,779,731 | Vaccination Syringe. |
| 2,894,138 | Prefillable Auto-Retractable Safety Syringe |
| 2,607,836 | Improved Controlled Retraction Syringe and Plunger Therefor |
| 2,406,567 | Single Use Syringe |
| 2,554,196 | Retractable Syringe with Plunger Disabling System |
| 2,107,631 | Retractable Syringe |
| 2,621,480 | Single Use Safety Syringe Having a Retractable Needle |
| 2,605,115 | Controlling the Retraction of a Needle in an Auto Retractable Syringe |
| 2,854,648 | Improved Retractable Syringe Needle |
| 2,762,847 | Syringe Adapter * |
| 2,963,334 | Retractable Syringe |
| 2,093,217 | Retractable Syringe |
| 2,845,362 | Auto-Injector for Retractable Syringe |
| 2,437,415 | Retractable Syringe with Reduced Retraction Force |
| 1,328,388 | Disposable Retractable Syringe |
| 2,843,477 | Automatic Reconstitution for Dual Chamber Syringe |
| 2,731,117 | A Retractable Syringe |
| 2,348,984 | Hypodermic Syringe with Selectively Retractable Needle |
| 2,604,322 | Controlled Retraction Syringe and Plunger Therefor |
| 2,559,089 | Single Use Retractable Syringe |
| 2,829,372 | Retractable Syringe with Locking Plunger |
| 2,829,355 | Retractable Syringe with Segmented Retaining Ledge |
| 2,601,431 | Auto Retractable Syringe |
| 2,806,218 | Dual Chamber Syringe with Retractable Needle |
| 2,930,095 | Dual Chamber Syringe with Retractable Needle |
| 2,806,216 | Dual Chamber Syringe with Retractable Needle |
| 2,806,215 | Dual Chamber Syringe with Retractable Needle |
| 2,806,036 | Dual Chamber Passive Retraction Needle Syringe |
| 2,914,028 | Actuation Mechanisms for Dual Chamber Mixing Syringes |
| 2,107,659 | Retractable Syringe ETC Needles |
| 2,580,092 | Single Use Pneumatic Safety Syringe with Retractable Needle |
| 2,862,880 | Plunger Sub-Assemblies and Auto-Injectors Having Low Retraction |

SUMMARY OF THE INVENTION

An automatic retractable syringe comprised of a syringe inside a compressed spring loaded locking safety sheath that moves into a protective position over the needle of the syringe utilizing a positional locking mechanism on the side of said safety sheath that in the open/ready (needle exposed) position retains said safety sheath with the needle of said syringe exposed for use, where the plunger does not trigger said locking mechanism when drawn outward from the barrel and when said plunger is depressed, the bottom of the plunger top depresses the mechanism trigger, closing the gap at position A and forcing said locking mechanism out of said position A, causing said locking mechanism to be under tension while displaced and the spring to expand and the locking safety sheath to move into its protective position, where a portion of said locking safety sheath covers the needle, causing said locking mechanism to move to position B, where said locking mechanism then locks in place in position B, preventing said locking safety sheath from further movement, said position B comprises an optional fusing system, said fusing system is comprised of an adhesive or bonding chemical contained in a protective but breakable coating, said locking-mechanism is protected by a tamperproof encasement, said needle is covered by a removable needle cap prior to use, said locking safety sheath is also comprised of a viewing port to enable clear viewing of the measurement notches on the syringe, a safety tab to prevent the safety feature of the retractable syringe from being triggered prior to use, stoppers to prevent the syringe from being separated from the safety sheath, and stabilizer guides to enable smooth and stable movement of the sheath and syringe and related moving parts in relation to each other, said safety syringe also comprises other basic components of a syringe, such as a needle adapter and needle hub.

OBJECTIVES OF THE INVENTION

The main objectives of this invention, is for use as a disposable safety syringe for distribution to those suffering from drug addiction, in order to protect others from injury or infectious disease from discarded infectious syringes, and for use as a safety precaution against injury or transmission of disease or contaminant in any situation where a syringe is required.

DESCRIPTION OF DRAWINGS

FIG. 3 shows the retractable syringe in its needle retracted position. The locking mechanism (3) has moved to position B (12) and the locking safety sheath (4) is now covering the needle (9) and is locked in place. When the optional fusing system (15) is utilized, said locking mechanism will now be permanently fixed in place at said position B (12).

FIG. 5a and FIG. 5b and demonstrates two of the possible variations of this locking mechanism and is meant to demonstrate that variations of this locking mechanism are possible. FIG. 5a and FIG. 5b are not intended to limit the many variations of this positional locking mechanism, as other variations are possible and should be included under the protection of this patent.

FIGURE LEGEND

Figure 1:
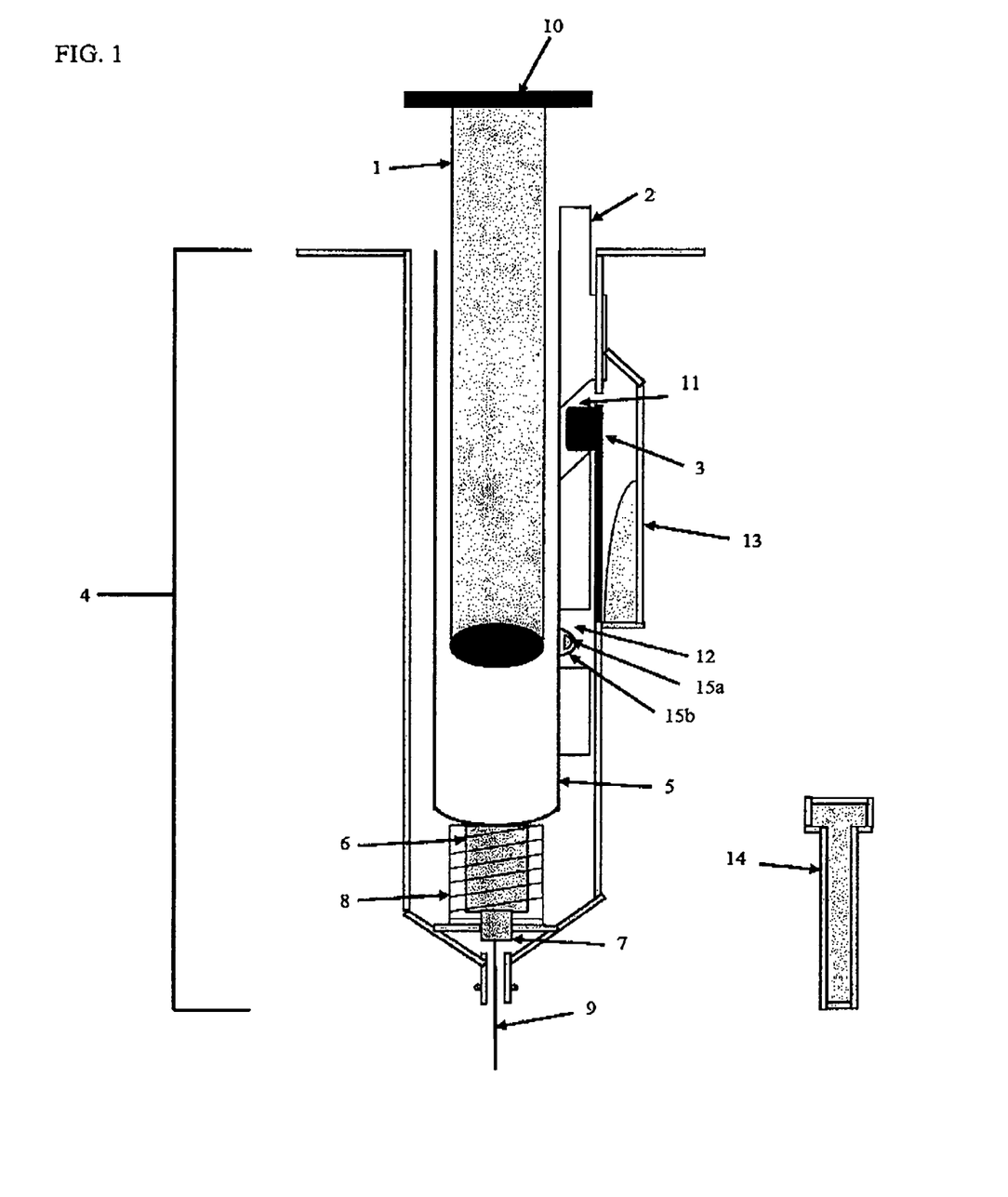
FIG. 1 shows the retractable syringe in its open/ready, or needle exposed position, where the locking mechanism (3) is located in position A (11) prior to use. The plunger of the syringe can be pulled outwards in order to draw materials into the barrel of the syringe without causing the locking mechanism to activate. When the plunger is depressed, it makes contact with said mechanism trigger (2), which activates the locking mechanism (3).
Figure 2:
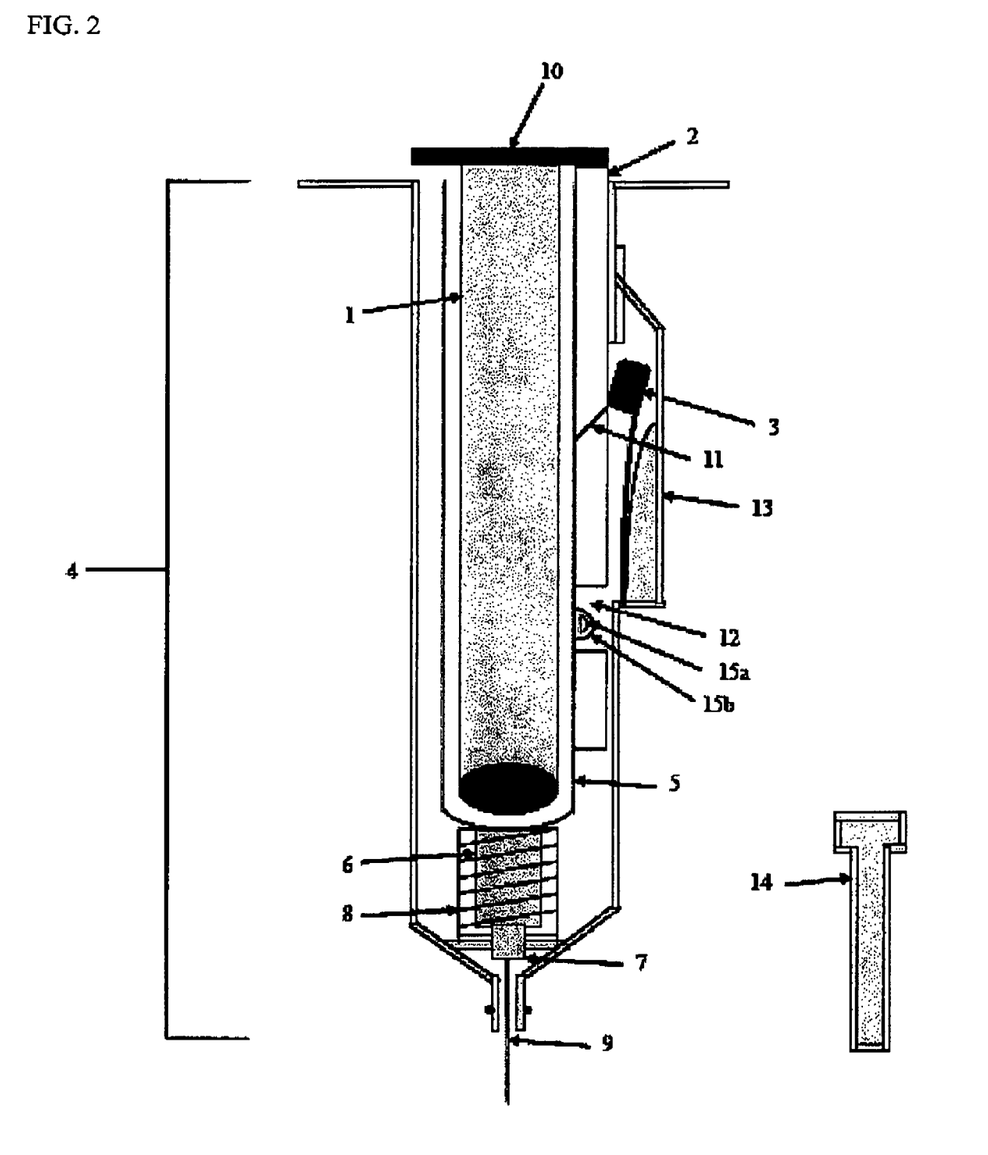
FIG. 2 shows the retractable syringe in its activated position, where the plunger (1) is depressed, and said mechanism trigger (2) has closed said position A (11), causing said locking mechanism (3) to be displaced and under tension. With the displacement of said locking mechanism from position A, the spring (8) is now activated and begins to expand. The locking safety sheath (4) can now move to its protective position, where it will cover the needle. The locking mechanism (3) can now move to protective position B (12).
Figure 3:
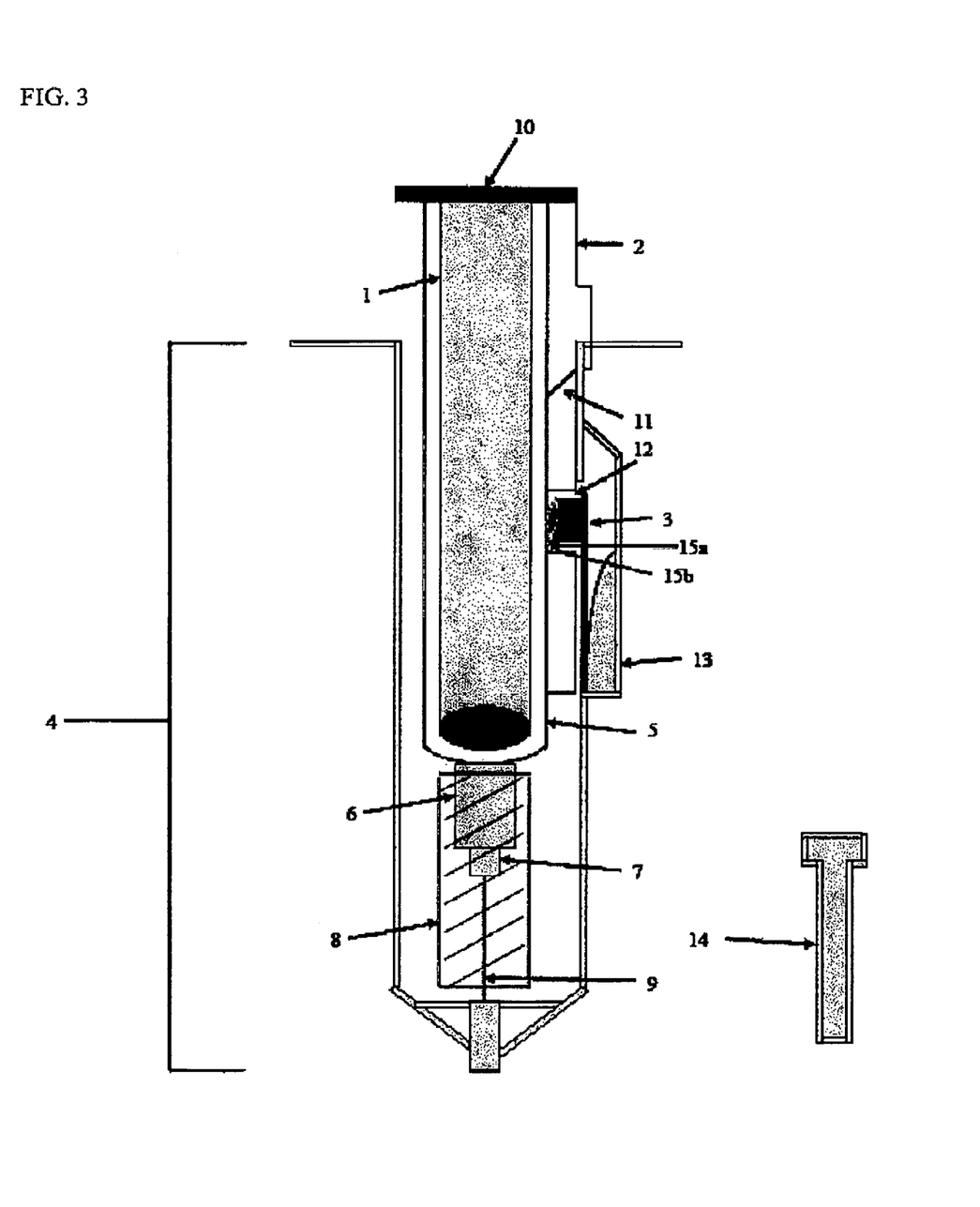
Figure 4:
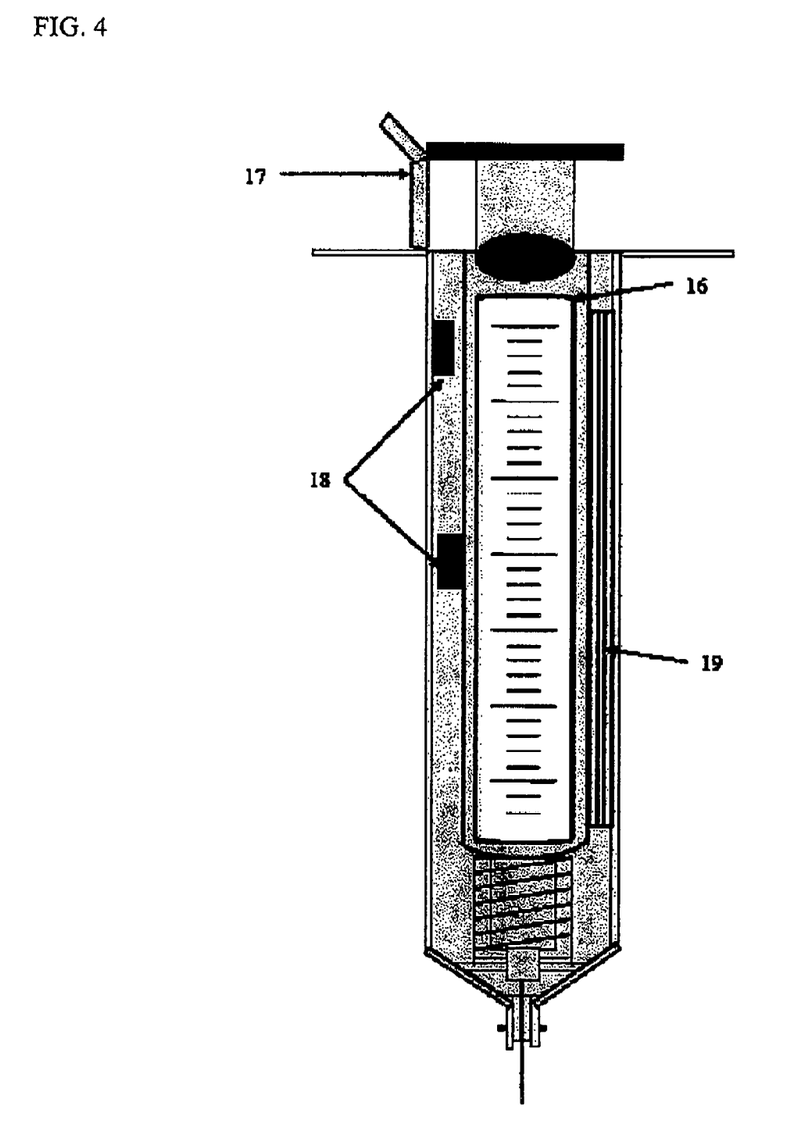
FIG. 4 shows the viewing port (16), safety tab (17), Stoppers (18), and stabilizer guides (19), which are not expressed in FIG. 1, 2, 3, or 5.
Figures 5A, 5B:
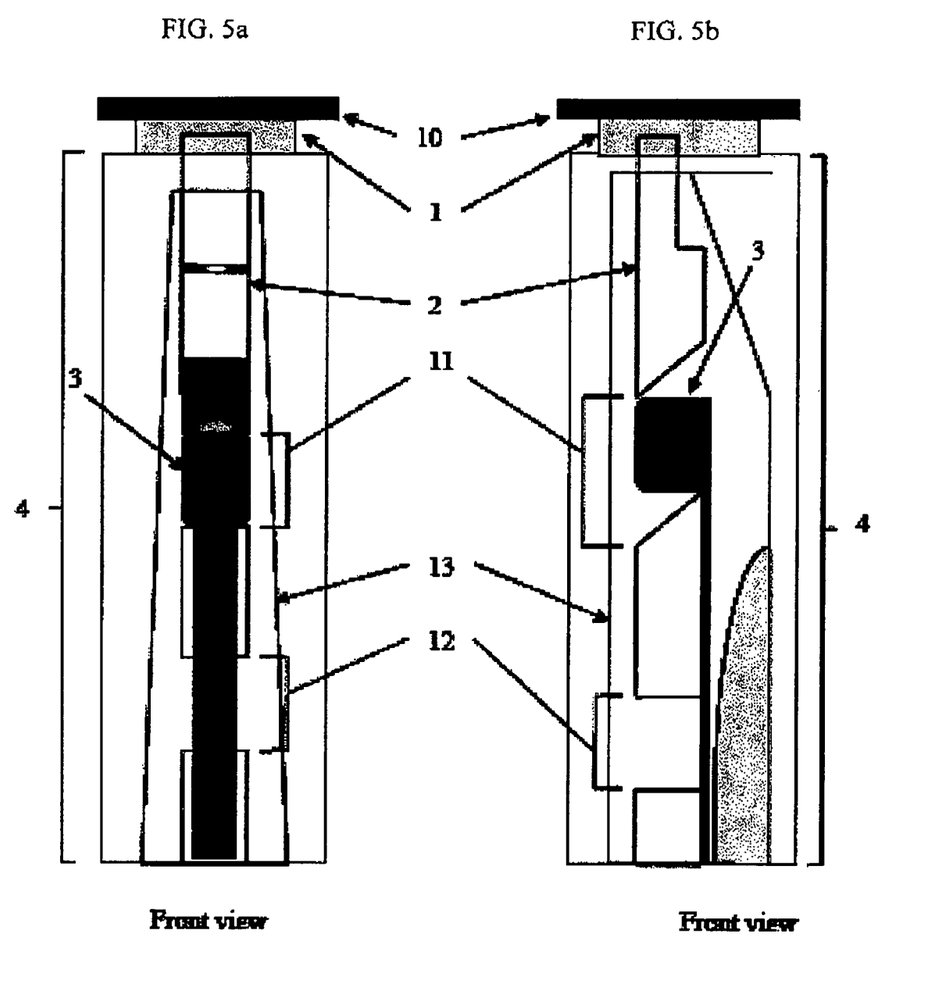
FIG. 5a shows said locking safety sheath as seen from the front view, wherein said locking mechanism, mechanism trigger, and all said related parts that aid in the action and positioning of said locking mechanism and the movement of said locking safety sheath are situated perpendicular relative to the safety locking sheath as seen in FIGS. 1, 2, and 3.
FIG. 5b shows said locking mechanism and related parts in an alternative design configuration, wherein said locking mechanism and related parts are positioned to the right (or can be arranged in a different variation or position) in design, allowing the locking mechanism and related parts to permit a slimmer design without changing the basic design concepts of said locking mechanism, locking safety sheath, and retractable syringe.

FIGS. 1, 2, 3, 4, 5a, and 5b contain a numbered listing of parts for the retractable syringe. The numbered parts are as follows:
1 Plunger
2 Mechanism Trigger
3 Locking Mechanism
4 Locking Safety Sheath
5 Barrel
6 Needle Adapter
7 Needle Hub
8 Spring
9 Needle
10 Plunger Top
11 Position A
12 Position B
13 Tamperproof Encasement
14 Needle Cap
15a and 15b Optional Fusing System
15a Adhesive or bonding chemical
15b Protective coating
16 Viewing port
17 Safety Tab
18 Stoppers
19 Stabilizer guides

DESCRIPTION OF THE INVENTION

An automatic retractable syringe comprised of a syringe inside a compressed spring loaded locking safety sheath (4) that moves into a protective position over the needle (9) of the syringe utilizing a positional locking mechanism (3) on the side of said safety sheath that in the open/ready (needle exposed) position retains said safety sheath with the needle of said syringe exposed for use, where the plunger (1) does not trigger said locking mechanism when drawn outward from the barrel (5) and when said plunger is depressed, the bottom of the plunger top (10) depresses the mechanism trigger (2), closing the gap at position A (11) and forcing said locking mechanism (3) out of said position A (11), causing said locking mechanism (3) to be under tension while displaced and the spring (8) to expand and the locking safety sheath (4) to move into its protective position, where a portion of said locking safety sheath covers the needle, causing said locking mechanism to move to position B (12), where said locking mechanism then locks in place in position B (12), preventing said locking safety sheath from further movement, said position B (12) comprises an optional fusing system (15a and 15b), said fusing system is comprised of an adhesive or bonding chemical (15a) contained in a protective but breakable coating (15b), said locking mechanism is protected by a tamperproof encasement (13), said needle is covered by a removable needle cap (14) prior to use, said locking safety sheath is also comprised of a viewing port (16) to enable clear viewing of the measurement notches on the syringe, a safety tab (17) to prevent the safety feature of the retractable syringe from being triggered prior to use, stoppers (18) to prevent the syringe from being separated from the safety sheath, and stabilizer guides (19) to enable smooth and stable movement of the sheath and syringe and related moving parts in relation to each other, said safety syringe also comprises other basic components of a syringe, such as a needle adapter (6) and needle hub (7).

This invention is distinct in comparison with prior art, as it has a unique automatic locking feature that is triggered simply by expelling the contents of the barrel with the depression of the plunger that causes the needle to retract only when the user releases the thumb pressure applied to the plunger top. The movement of the locking safety sheath works in such a way that the needle is covered by a portion of the locking safety sheath when it locks into place at position B. Prior art has been previously designed such that the needle retracts into the syringe itself. This invention is unique in that the needle does not retract into the barrel of the syringe, but instead the method of retraction occurs through the movement of the safety locking sheath over the needle. The various safety features, such as the automatic locking safety sheath, helps protect from injury, or infectious diseases the syringe may be contaminated with. The locking safety features of this retractable syringe are unique to other prior art and is an improvement over other attempts to create a retractable syringe for safety purposes, as this safety syringe is designed to be used by not only those in the field of medicine, but also by people who do not have adequate medical training. Once locked, the syringe can be handled safely without the risk or danger of injury. The process of making this retractable syringe will be similar to that of making any other style of hypodermic needle or syringe. The needle is produced from steel that is heated and formed to make the needle, and a bevel is formed on the end during this process. Some needles are formed by using a die casting.

There are various ways that the barrel, plunger, and locking safety sheath can be made, including extrusion and injection molding. Assembly of the syringe is carried out using specialized automated machines and/or manually. After assembly, the syringes are put into packaging in order to keep them sterilized prior to use.

The simplicity of the design of this retractable syringe will make this invention less expensive to make compared to prior art and this design incorporates the mechanism parts on the outside of the syringe in order to ensure the syringe maintains its autonomy to minimize internal surface area in which contamination might be able to form in order to create the most sterile conditions possible for the interior working parts of the syringe.

This invention makes it easier for the handler to identify the syringe as a proper safety syringe simply by sight, due to the external design of the locking safety sheath, whereas other designs cannot readily be identified by sight alone.

This invention also allows the user to control the retraction of the syringe with minimal effort, as the force used to depress the plunger and activate the locking safety sheath transfers automatically to countering the force released by the compressed spring.

This invention prevents splatter or backsplash, and will significantly reduce pain due to the retraction of the needle as the function of the needle is autonomous to the locking mechanism and safety sheath and therefore can operate independently without the design of the locking mechanism and safety sheath impeding on the function of the syringe.

The design of this invention allows it to be identifiable by sight for safety reasons. Finally, the design of this invention protects the handler of a used retractable syringe in order for the syringe to be discarded safely.

The invention claimed is:

1. A retractable syringe comprising:
   a syringe barrel with an open forward end, a rearward end, a first area on a side of the barrel at position A, a second area on the side of the barrel at position B, the second area including a fusing system comprising an adhesive or bonding chemical contained in a breakable protective coating;
   a plunger having a plunger top, the plunger being configured to be placed in the barrel with the plunger top extending out of the rearward end;
   a needle adapter including a needle hub with a needle, the needle adapter placed at the forward end of the barrel;
   a mechanism trigger, the mechanism trigger is configured to engage an underside of the plunger top and activate the retraction of the needle;
   a locking safety sheath having a spring and a locking mechanism, the locking mechanism having a first position without being under tension and a second position being under tension; and
   wherein the retractable syringe is configured such that during locking of the safety sheath to prevent exposure of the needle:
     the plunger top engages the mechanism trigger and moves the mechanism trigger into the first area at position A;
     upon movement of the mechanism trigger into the first area at position A, the locking mechanism moves from the first position to the second position allowing the spring to expand and causing downward movement of the locking mechanism and safety sheath, and retraction of the needle;
     upon downward movement of the locking mechanism, the locking mechanism moves into the second area, breaking the protective coating and releasing the adhesive or chemical bond in order to fuse the locking mechanism in the second area and prevent further movement between the locking mechanism and the safety sheath.

2. The retractable syringe as claimed in claim 1, wherein said plunger is configured to be pulled upwards to draw contents to be administered without activating the mechanism trigger, and the plunger is configured when depressed and upon reaching the bottom of the barrel, the contents will be administered completely and the mechanism trigger will be activated.

3. The retractable syringe as claimed in claim 1, further comprising a tamper proof encasement covering the locking mechanism, the tamper proof encasement is configured to protect the locking mechanism from being damaged or tampered with and aids in the stability and strength of said locking mechanism.

4. The retractable syringe as claimed in claim 1, further comprising a removable protective needle cap.

5. The retractable syringe as claimed in claim 1, wherein, the locking safety sheath has a viewing port on the side of the safety sheath.

6. The retractable syringe as claimed in claim 1, wherein a safety tab is attached to said plunger top and to the locking safety sheath or to the barrel, in order to prevent premature activation of the locking mechanism during transport or prior to use, and the safety tab is configured to be removed and discarded prior to using the retractable syringe.

7. The retractable syringe as claimed in claim 1, wherein said the syringe barrel of the syringe comprises two notched positions.

8. The retractable syringe as claimed in claim 1, wherein the locking safety sheath and the syringe barrel comprise stoppers located on opposing sides, on the locking safety sheath and on the barrel of the syringe, the stoppers are configured to move towards each other when the locking safety sheath is activated, the stoppers are configured act to prevent the syringe barrel from being removed from the locking safety sheath.

9. The retractable syringe as claimed in claim 1, wherein the locking safety sheath and the syringe barrel comprise stabilizer guides the stabilizer guides are configured to aid in the stability of movement of the syringe barrel inside the locking safety sheath and prevents binding while the locking safety sheath and the syringe barrel are in motion.

* * * * *